United States Patent [19]

Maurer et al.

[11] 4,332,745
[45] Jun. 1, 1982

[54] PREPARATION OF 2-CYANO-3,3-DIMETHYL-CYCLOPROPANE-1-CARBOXYLIC ACID ESTERS AND INTERMEDIATES THEREFOR

[75] Inventors: Fritz Maurer; Hans-Jochem Riebel, both of Wuppertal; Uwe Priesnitz, Unna-Massen, all of Fed. Rep. of Germany

[73] Assignee: Bayer Aktiengesellschaft, Leverkusen, Fed. Rep. of Germany

[21] Appl. No.: 153,298

[22] Filed: May 27, 1980

[30] Foreign Application Priority Data

Jun. 12, 1979 [DE] Fed. Rep. of Germany ....... 2923777

[51] Int. Cl.$^3$ ................ C07C 120/00; C07C 121/46; C07C 121/16
[52] U.S. Cl. ................................ 260/464; 260/465.4; 562/506
[58] Field of Search .......................... 260/464

[56] References Cited

U.S. PATENT DOCUMENTS

| | | | |
|---|---|---|---|
| 4,174,347 | 11/1979 | Austermuhle-Bertola | 260/464 |
| 4,195,033 | 3/1980 | Punja | 260/464 |
| 4,198,347 | 4/1980 | Punja | 260/464 |
| 4,205,009 | 5/1980 | Onore et al. | 260/464 |
| 4,211,720 | 7/1980 | Austermühle-Bertola | 260/464 |

OTHER PUBLICATIONS

Devos, et al., Tetrahedron Letters, No. 21, (1978), pp. 1847–1850.
Derwent, Japanese Patents Gazette, Section Ch: Chemical, A43 Agricultural Chemistry-p. 5, J5–C, (1978).
Kristensen, et al., Bull. Soc. Chim. Belg., 87, (1978), pp. 721–732.
Remy, et al., Tetrahedron Letters No. 21, (1979), pp. 1847–1850.
Elliott, et al., Pestic. Sci., (1976), 7, pp. 492–498.
Perkin, et al., J. Chem. Soc. (London), 75, (1899), pp. 48–59.

*Primary Examiner*—Joseph Paul Brust
*Attorney, Agent, or Firm*—Sprung, Horn, Kramer & Woods

[57] ABSTRACT

A process for the preparation of a 2-cyano-3,3-dimethyl-cyclopropane-1-carboxylic acid ester of the formula

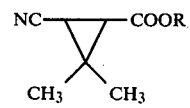

in which
R is optionally substituted alkyl, comprising reacting a 3-halogeno-3-cyano-2,2-dimethyl-propane-1-carboxylic acid ester of the formula

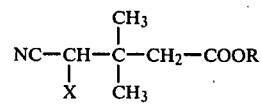

in which
X is halogen, with a base at a temperature from about 0 to 100° C. The starting esters are new and may be prepared by halogenating a compound of the formula

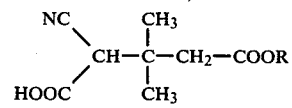

and decarboxylating.

6 Claims, No Drawings

PREPARATION OF 2-CYANO-3,3-DIMETHYL-CYCLOPROPANE-1-CARBOXYLIC ACID ESTERS AND INTERMEDIATES THEREFOR

The invention relates to an unobvious process for the preparation of certain 2-cyano-3,3-dimethyl-cyclopropane-1-carboxylic acid esters, some of which are known, to certain 3-halogeno-3-cyano-2,2-dimethyl-propane-1-carboxylic acid esters, as new intermediate products in this process, and to a process for their preparation.

It is already known that 3,3-dimethyl-cyclopropane-1,2-dicarboxylic acid (caronic acid) is obtained when 2,2-dimethyl-propane-1,3-dicarboxylic acid anhydride ($\beta,\beta$-dimethyl-glutaric anhydride) is reacted successively with phosphorus pentabromide, bromine and alcohol, the 1-bromo-2,2-dimethyl-propane-1,3-dicarboxylic acid ester thereby formed is treated with potassium carbonate in alcohol, the residue is dissolved in water, after distilling off the alcohol, and the product is extracted with ether, after acidification (see J. Chem. Soc. (London) 75 (1899), 49–61).

This caronic acid synthesis has the disadvantage that in addition to the 1-bromo-2,2-dimethyl-propane-1,3-dicarboxylic acid ester, about 20–30% of the 1,3-dibromo-2,2-dimethyl-1,3-dicarboxylic acid ester is obtained as a by-product in the bromination stage and cannot be separated off cleanly. The yield of the desired product is thereby greatly reduced. Another disadvantage of the aforesaid synthesis method is the use of the expensive reagents phosphorus pentabromide and bromine.

It is also known that 2-cyano-3,3-dimethyl-cyclopropane-1-carboxylic acid esters, which can easily be saponified to give caronic acid, are obtained when 2-cyano-3,3-dimethyl-cyclopropane-1,1-dicarboxylic acid esters are decarboxylated (see Japanese Patent Specification 53 108951 and Bull. Soc. Chim. Belg. 87 (1978) 721–732). However, the yields in this process are also unsatisfactory.

The present invention now provides:

(1) a process for the preparation of a 2-cyano-3,3-dimethylcyclopropane-1-carboxylic acid ester of the general formula

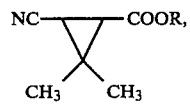

in which
R represents optionally substituted alkyl, characterized in that a 3-halogeno-3-cyano-2,2-dimethylpropane-1-carboxylic acid ester of the general formula

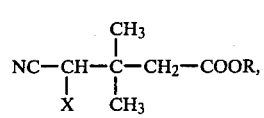

in which
R has the meaning indicated above and
X represents halogen, is reacted with a base, if appropriate in the presence of a diluent, at a temperature from about 0° to 100° C.;

(2), as new compounds, the 3-halogeno-3-cyano-2,2-dimethylpropane-1-carboxylic acid esters of the general formula

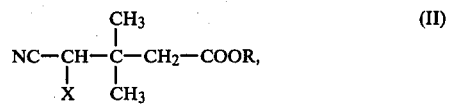

in which
R represents optionally substituted alkyl and
X represents halogen; and (3) a process for the preparation of a 3-halogeno-3-cyano-2,2-dimethyl-propane-1-carboxylic acid ester of the formula (II) above, characterized in that a 3-carboxy-3-cyano-2,2-dimethyl-propane-1-carboxylic acid ester of the general formula

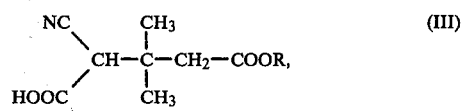

in which
R has the meaning indicated above, is reacted with a halogenating agent, if appropriate in the presence of an acid acceptor and if appropriate using a diluent, at a temperature from about $-20°$ to $+100°$ C., and the halogenation product, formed as an intermediate, of the general formula

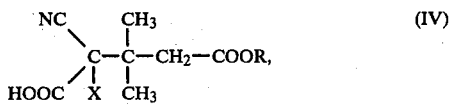

in which
R and X have the meanings indicated above, is decarboxylated by heating to a temperature from about 80° to 250° C.

Surprisingly, 2-cyano-3,3-dimethyl-cyclopropane-1-carboxylic acid esters of the formula (I) can be prepared in good yields and in high purity in a considerably simpler and less expensive manner by process (1) according to the invention than by known methods. Caronic acid, which can be used as an intermediate product from pyrethroids, is obtained from these esters in almost quantitative yield in a simple saponification reaction.

If, for example, 3-chloro-3-cyano-2,2-dimethyl-propane-1-carboxylic acid methyl ester is used as the starting substance and sodium methylate is used as the base in process (1), the course of the reaction can be outlined by the following equation:

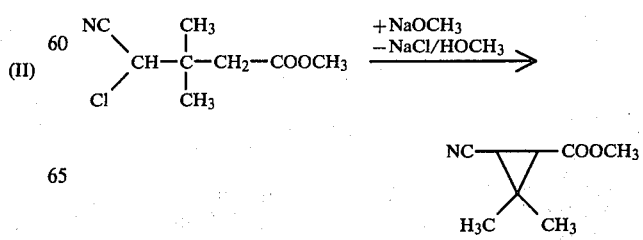

Formula (II) provides a definition of the new 3-halogeno-3-cyano-2,2-dimethyl-propane-1-carboxylic acid esters to be used as starting compounds in process (1). Preferably, in this formula, R represents $C_1$-$C_4$-alkyl (especially methyl, ethyl or isopropyl), and X represents chlorine or bromine.

Examples of the compounds (II) which may be mentioned are: 3-chloro-3-cyano-2,2-dimethyl-propane-1-carboxylic acid methyl ester, ethyl ester, n-propyl ester, iso-propyl ester, n-butyl ester, iso-butyl ester and tert.-butyl ester, and 3-bromo-3-cyano-2,2-dimethyl-propane-1-carboxylic acid methyl ester, ethyl ester, n-propyl ester, iso-propyl ester, n-butyl ester, iso-butyl ester, sec.-butyl ester and tert.-butyl ester.

Process (1) is preferably carried out using a diluent. Preferred diluents are water and/or polar organic solvents. These include, as preferences, carboxylic acid amides, for example dimethylformamide and N-methyl-pyrrolidone; sulphoxides and sulphones, for example dimethylsulphoxide and tetramethylenesulphone; phosphoric acid amides, for example hexamethylphosphoric acid triamide; ethers for example glycol dimethyl ether, diglycol dimethyl ether, tetrahydrofuran and dioxane; nitriles, for example acetonitrile and propionitrile; and alcohols, for example methanol, ethanol, n- and iso-propanol and n-, iso-, sec.- and tert.-butanol. The latter are particularly preferred as diluents for process (1).

In general, the reaction temperature is kept between 0° and 100° C., preferably between 10° and 80° C., in process (1). The reaction is in general carried under normal pressure or under a pressure chosen to suit the vapor pressure of the diluent.

The customary acid-binding agents can be used as bases in process (1). Particularly suitable bases are alkali metal carbonates and alcoholates, such as sodium methylate or ethylate and potassium methylate or ethylate, and furthermore aliphatic, aromatic or heterocyclic amines, for example triethylamine, trimethylamine, dimethylaniline, dimethylbenzylamine, pyridine and diazobicyclononane.

In general, between 1 and 1.5 mols, preferably between 1.05 and 1.3 mols, of base are employed per mol of 3-halogeno-3-cyano-2,2-dimethyl-propane-1-carboxylic acid ester of the formula (II).

In a preferred embodiment of the process according to the invention, the 3-halogeno-3-cyano-2,2-dimethyl-propane-1-carboxylic acid ester (II) is dissolved in one of the diluents indicated above, and the base, which is dissolved in one of the diluents indicated above, if appropriate, is added dropwise to this solution. The complete reaction mixture is stirred at a temperature between 40° and 70° C. for some hours.

Working up is effected in the customary manner: water is added to the reaction mixture and the mixture is extracted with a water-immiscible organic solvent, for example methylene chloride. The organic phase is washed with dilute hydrochloric acid and with water, dried and filtered and the filtrate is concentrated. The crude product which remains can be purified by vacuum distillation. The boiling point is used for its characterization.

The 2-cyano-3,3-dimethyl-cyclopropane-1-carboxylic acid esters to be prepared by process (1) can be converted into 3,3-dimethyl-cyclopropane-1,2-dicarboxylic acid (caronic acid) by hydrolysis, for example by heating to temperatures between 80° and 120° C. with alkali metal hydroxide solutions, for example 15 percent strength sodium hydroxide solution, and then acidifying the mixture at room temperature with a strong acid, for example hydrochloric acid. Caronic acid is thereby obtained as crystals and can be isolated by filtration.

Caronic acid or esters thereof can be used as intermediate products for the preparation of insecticidally and acaricidally active pyrethroids (see Pestic. Sci. 7 (1976), 492–498; and Tetrahedron Lett. 1978, 1847–1850).

If, for example, 3-carboxy-3-cyano-2,2-dimethylpropane-1-carboxylic acid methyl ester is used as the starting compound, chlorine is used as the halogenating agent and sodium acetate is used as the acid acceptor in process (3), the course of the reaction can be outlined by the following equation:

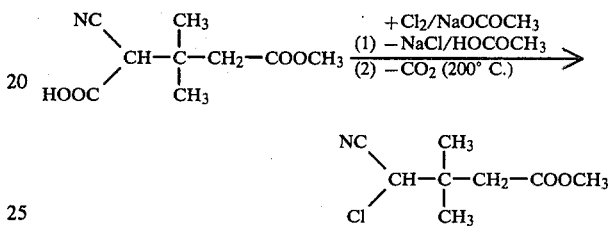

The new 3-halogeno-3-cyano-2,2-dimethyl-propane-1-carboxylic acid esters are obtained by the process described above, under (3), by reacting 3-carboxy-3-cyano-2,2-dimethyl-propane-1-carboxylic acid esters of the formula (III) above with a halogenating agent, if appropriate in the presence of an acid acceptor and if appropriate using a diluent, preferably water, at a temperature between −20° and +100° C., preferably between 0° and 50° C., and then decarboxylating the halogenation product, formed as an intermediate, of the formula (IV) above by heating to a temperature between 150° and 250° C., preferably between 180° and 220° C.

Examples which may be mentioned of halogenating agents which can be used in process (3) are bromine, chlorine and sulphuryl chloride. Bromine or chlorine is preferably used.

As acid acceptors which can be used in process (3) there may be mentioned alkali metal hydroxides, for example sodium hydroxide, potassium hydroxide and calcium hydroxide, alkali metal oxides, carbonates or bicarbonates and alkaline earth metal oxides, carbonates or bicarbonates, such as calcium oxide and carbonate, and furthermore alkali metal acetates, for example sodium acetate and potassium acetate. The latter are preferably used.

In a preferred embodiment of process (3), the 3-carboxy-3-cyano-2,2-dimethyl-propane-1-carboxylic acid ester of the formula (III) to be employed as the starting compound is initially introduced into water with 2 to 3 mol equivalents of one of the above-mentioned acid acceptors, and 1 to 1.5, preferably 1.05 to 1.3, mol equivalents of halogenating agent (bromine or chlorine) are metered in at a temperature from about 0° to 50° C., while stirring. After stirring the complete reaction mixture for several hours, it is acidified with a strong acid, for example hydrochloric acid, and extracted with a water-immiscible solvent, for example methylene chloride. After drying and filtering, the organic phase is concentrated and the residue is introduced dropwise into a flask heated to about 180° to 220° C. The decarboxylation product of the formula (II) thereby formed can be isolated in a pure form by vacuum distillation.

Formula (III) provides a definition of the 3-carboxy-3-cyano-2,2-dimethyl-propane-1-carboxylic acid esters to be employed as starting substances in process (3). Preferably, in this formula, R represents $C_1$-$C_4$-alkyl, especially methyl, ethyl, or isopropyl.

Examples which may be mentioned are: 3-carboxy-3-cyano-2,2-dimethyl-propane-1-carboxylic acid methyl ester ethyl ester, n-propyl ester, iso-propyl ester, n-butyl ester, iso-butyl-ester, sec.-butyl ester and tert.-butyl ester.

3-Carboxy-3-cyano-2,2-dimethyl-propane-1-carboxylic acid esters of the formula (III) are known (see J. Chem. Soc. (London) 75 (1899), 49–61).

ILLUSTRATIVE EXAMPLES

EXAMPLE 1

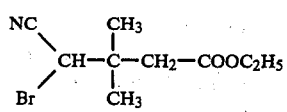

40 g (0.25 mol) of bromine were added dropwise to a solution of 42.6 g (0.2 mol) of 3-carboxy-3-cyano-2,2-dimethyl-propane-1-carboxylic acid ethyl ester and 41 g of sodium acetate in 400 ml of water at 20° C. The mixture was subsequently stirred at 20° C. for 5 hours. It was then acidified with dilute HCl and extracted twice with 100 ml of methylene chloride each time. The organic solutions were dried over sodium sulphate and then concentrated. The residue was first introduced dropwise into a flask, which was heated to 200° C., whereupon continuous evolution of $CO_2$ started, and was then twice subjected to fractional distillation. 38 g (76.5% of theory) of 3-bromo-3-cyano-2,2-dimethyl-propane-1-carboxylic acid ethyl ester were obtained in the form of a colorless oil of boiling point 92°–95° C./2.5 mm Hg.

EXAMPLE 2

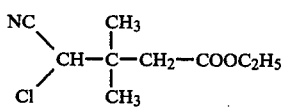

17.8 g (0.25 mol) of chlorine were passed into a solution of 42.6 g (0.2 mol) of 3-carboxy-3-cyano-2,2-dimethyl-propane-1-carboxylic acid ethyl ester and 41 g of sodium acetate in 400 ml of water at 20° C. The mixture was subsequently stirred at 20° C. for 5 hours and then acidified with dilute HCl. The acid solution was worked up as described under Example 1. 28 g (69% of theory) of 3-chloro-3-cyano-2,2-dimethyl-propane-1-carboxylic acid ethyl ester were obtained in the form of a colorless oil of boiling point 80°–82° C./1 mm Hg.

EXAMPLE 3

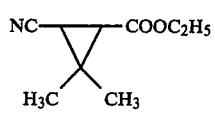

14.8 g (0.12 mol) of diazobicyclononane were added dropwise to a solution of 24.8 g (0.1 mol) of 3-bromo-3-cyano-2,2-dimethyl-propane-1-carboxylic acid ethyl ester in 100 ml of alcohol at 20° C. The mixture was then warmed to 50°–60° C. for 3 hours and cooled to 20° C., and 200 ml of water were added to the reaction mixture. The mixture was extracted twice with 100 ml of methylene chloride each time. The combined methylene chloride extracts were washed twice with 50 ml of 5% strength hydrochloric acid each time and twice with 50 ml of water each time, dried over sodium sulphate and concentrated. The residue was fractionated. 12.5 g (75% of theory) of 2-cyano-3,3-dimethyl-cyclopropane-1-carboxylic acid ethyl ester were obtained in the form of a colorless oil of boiling point 62°–64° C./1 mm Hg.

EXAMPLE 4

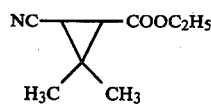

8.15 g (0.12 mol) of sodium ethylate in 30 ml of ethanol were added dropwise to a solution of 24.8 g (0.1 mol) of 3-bromo-3-cyano-2,2-dimethyl-propane-1-carboxylic acid ethyl ester in 50 ml of ethanol. The mixture was subsequently stirred at 50°–60° C. for 3 hours. 200 ml of water were then added and the reaction mixture was neutralized with HCl and extracted twice with 50 ml of methylene chloride each time. The combined methylene chloride extracts were washed twice with 50 ml of $H_2O$ each time, dried over $Na_2SO_4$ and then concentrated. The residue was fractionated. 11.5 (69% theory) of 2-cyano-3,3-dimethyl-cyclopropane-1-carboxylic acid ethyl ester were obtained in the form of a colorless oil of boiling point 68°–72° C./2 mm Hg.

EXAMPLE 5

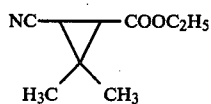

8.15 g (0.12 mol) of sodium ethylate were added dropwise to a solution of 20.3 g (0.1 mol) of 3-chloro-3-cyano-2,2-dimethyl-propane-1-carboxylic acid ethyl ester in 500 ml of ethanol. The mixture was subsequently stirred at 60° C. for 4 hours and then worked up as described in Example 4. Yield: 14 g (84% of theory) of 2-cyano-3,3-dimethyl-cyclopropane-1-carboxylic acid ethyl ester.

EXAMPLE 6

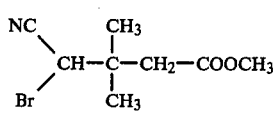

3-Bromo-3-cyano-2,2-dimethyl-propane-1-carboxylic acid methyl ester could be prepared in a yield of 75% of theory analogously to Example 1 (boiling point: 83° C./1 mm Hg).

EXAMPLE 7

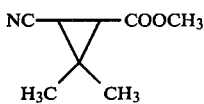

2-Cyano-3,3-dimethyl-cyclopropane-1-carboxylic acid methyl ester could be prepared in a yield of 75% of theory from the bromide in Example 6 and sodium methylate, as the base, analogously to Example 4 (boiling point: 62° C./1 mm Hg).

EXAMPLE 8

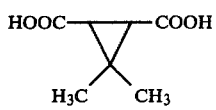

A mixture of 50 ml of 15 percent strength sodium hydroxide solution and 8.5 g (0.05 mol) of 3,3-dimethyl-2-cyano-cyclopropane-1-carboxylic acid ethyl ester was boiled under reflux for 18 hours. The mixture was then cooled to 10° C., concentrated hydrochloric acid was added until the pH value had reached about 2 and the mixture was then cooled in an ice-bath for 1 hour. The product which had precipitated was filtered off and rinsed with ice-water. 7.3 g (92% of theory) of trans-3,3-dimethylcyclopropane-1,2-dicarboxylic acid were thus obtained in the form of a colorless powder with a melting point of 217° C.

It will be appreciated that the instant specification and examples are set forth by way of illustration and not limitation, and that various modifications and changes may be made without departing from the spirit and scope of the present invention.

What is claimed is:

1. A process for the preparation of a 2-cyano-3,3-dimethyl-cyclopropane-1-carboxylic acid ester of the formula

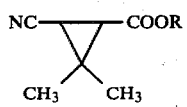

in which
R is alkyl,
comprising reacting a 3-halogeno-3-cyano-2,2-dimethylpropane-1-carboxylic acid ester of the formula

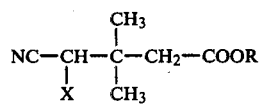

in which
X is chlorine or bromine,
with a base at a temperature from about 0° to 100° C.

2. A process according to claim 1, in which R is $C_1$–$C_4$-alkyl.

3. A process according to claim 1, in which the reaction is effected in the presence of an inert diluent comprising water and/or a polar organic solvent.

4. A process according to claim 3, in which the diluent is an alcohol.

5. A process according to claim 1, wherein about 1 to 1.5 mols of an alkali metal carbonate, an alkali metal alcoholate or an aliphatic, aromatic carbocyclic or heterocyclic amine are employed as base per mole of ester.

6. A process according to claim 5, in which R is $C_1$–$C_4$-alkyl, the reaction is effected in the presence of an alcohol as diluent, at about 10° to 80° C. and about 1.05 to 1.3 mols of base are employed per mol of ester.

* * * * *